United States Patent [19]
Ohishi

[11] Patent Number: 5,442,179
[45] Date of Patent: Aug. 15, 1995

[54] PHOTOMULTIPLIER ASSEMBLY AND GAMMA CAMERA HEAD

[75] Inventor: Keiichi Ohishi, Hamamatsu, Japan

[73] Assignee: Hamamatsu Photonics, K.K., Hamamatsu, Japan

[21] Appl. No.: 122,957

[22] Filed: Sep. 20, 1993

[30] Foreign Application Priority Data

Sep. 21, 1992 [JP] Japan .................. 4-251282

[51] Int. Cl.6 .................... 250 366; 250 368
[52] U.S. Cl. .................... 250/363.02
[58] Field of Search .................... G01T 1/20

[56] References Cited

U.S. PATENT DOCUMENTS

| | | | |
|---|---|---|---|
| 3,919,556 | 11/1975 | Berninger | 250/366 |
| 4,047,034 | 9/1977 | Auphan | 250/354.1 |
| 4,284,891 | 8/1981 | Pergrale et al. | 250/363.02 |
| 4,306,171 | 12/1981 | Faulkner et al. | 313/533 |
| 4,582,994 | 5/1986 | Berg | 250/363.10 |
| 4,837,439 | 6/1989 | Genna et al. | 250/368 |

FOREIGN PATENT DOCUMENTS 2286393 4/1976 France .
2-266287 10/1990 Japan .
2-304316 12/1990 Japan .

*Primary Examiner*—Constantine Hannaher
*Attorney, Agent, or Firm*—Cushman Darby & Cushman

[57] ABSTRACT

A photomultiplier assembly for use in gamma cameras, for example, includes an array of head-on type photomultipliers disposed in parallel relation to one another. The array of photomultipliers has a plurality of dead spaces, in which reflectors are respectively disposed. The reflector can reflect light which has entered the corresponding dead space to an upper portion of a side wall of aproximate photomultiplier. A side photocathode surface is formed on an inside surface of the upper portion of the side wall of the photomultiplier. Therefore, the light which has entered the dead space is reflected by the reflector and impinges on the side photocathode surface to be converted into photoelectrons.

21 Claims, 13 Drawing Sheets

PHOTOMULTIPLIER ASSEMBLY AND GAMMA CAMERA HEAD

BACKGROUND OF THE INVENTION

1. Field of the Invention

The present invention relates to a photomultiplier assembly for use in cameras for detecting gamma rays, high sensitivity photometering devices for metering feeble light, etc.

2. Related Background Art

Recently, in the field of nuclear medicine, a diagnostic method in which radioisotope is given to a patient to measure a distribution image of the radioisotope has been rapidly developed. In this diagnostic method, gamma cameras for detecting gamma rays emitted from the radioisotope are generally used to obtain distribution images of the radioisotope those cameras being referred to as gamma cameras.

FIG. 1 is a vertical sectional view schematically showing one example of the detection units of the conventional generally used gamma cameras, i.e., gamma camera heads as shown in "Journal of Japanese Association of Radiation Techniques", March, 1971, p. 40. This gamma camera head 1 includes a box-shaped lead shield or lead housing 2 with one side opened. In the lead housing 2, there is a photomultiplier assembly 3 comprising a plurality of photomultipliers 4 held in a predetermined two-dimensional array. A collimator 5 is disposed in the opening of the lead housing 2. This collimator 5 comprises a lead plate with a great number of pores formed in parallel therethrough. Between the collimator 5 and the photomultiplier assembly 3, there are provided a scintillator 6 of sodium iodide and a light guide 7.

In such a gamma camera head 1, gamma rays entering in substantially parallel with the pores of the collimator 5 are incident on the scintillator 6, and the scintillator 6 emits light. As seen in FIG. 2 enlarging a part Of the light guide 7 and the photomultiplier assembly 3 with the scintillator not shown, light (solid lines) from the scintillator 6 passes through the light guide 7 and enters the photocathode surfaces 8 of the respective photomultipliers 4 arranged in a honeycomb structure behind the light guide 7. When the light arrives at the photocathode surfaces 8, photoelectrons are emitted, and the photoelectrons are multiplied gradually by groups of dynodes (not shown) in the photomultipliers 4 by the secondary electron emitting effect. The multiplied electrons are taken out as output pulse signals from an anode (not shown).

In this case, the most proximate of the photomultipliers to incident positions of the gamma rays receives a largest quantity of light. The photomultipliers which are more distant from the incident positions of the gamma rays receive the smaller quantities of light. Quantities of light distributed to the respective photomultipliers 4 are proportional to solid angles defined by light emitting points and the photocathode surfaces of the respective photomultipliers 8 as to those of the photomultipliers near the light emitting points. When the respective photomultipliers 4 receive the light, they output pulse signals with wave crests proportional to their incident light quantities. Accordingly, output signals of the photomultipliers 4 are larger as the photomultipliers 4 are located closer to incident positions of the gamma rays, and smaller as the photomultipliers are located more distant from incident positions of the gamma rays.

Accordingly, large and small signals from the respective photomultipliers disposed in a certain array are compared and computed by a position computing matrix circuit 9 disposed in the lead housing 2 so that incident positions of gamma rays are indicated by X-Y coordinate signals. Based on this coordinate signals, luminescent points can be generated at positions corresponding to the incident positions of gamma rays on a screen of a display device (not shown). The luminescent points on the screen are imaged by an optical camera to be accumulated on a frame of film. Thus, a scintigram related to a distribution of radioisotope in a patient's body can be recorded.

Such a gamma camera head 1 is not only for giving the two-dimensional distribution image of radioisotope, but also is used in a single photon emission computer tomography (SPECT).

In the photomultiplier assembly 3 of the gamma camera head 1 described above, when the photocathode surfaces 8 of the respective photomultipliers 4 are circular, as shown in a transverse cross section of the gamma camera head 1 of FIG. 3, gaps or dead spaces 10a, 10b are defined respectively among adjacent three photomultipliers, and between the inside surface of the lead housing 2 and the peripheral photomultipliers. Light which has entered these dead spaces 10a, 10b is not used. Resultant problems are that the condensing efficiency is accordingly lowered, and a resolution of the gamma camera is lowered.

To solve these problems, conventionally as shown in FIGS. 1 and 2, triangular pyramidal cuts or recesses are formed in a light guide 7 at positions corresponding to the dead spaces 10a, 10b, and triangular pyramidal reflectors 11a, 11b are placed in the recesses. In this arrangement, as shown in FIG. 2, light entering the respective dead spaces 10a, 10b reflects on the surfaces of the reflectors 11a, 11b, a part of the light enters the photocathode surfaces 8.

However, in the gamma camera head 1 with the reflectors 11a, 11b disposed in the light guide 7, as seen in FIG. 2, the peripheral edges of the photocathode surfaces of the photomultipliers 4 partially overlap the bottoms of the reflectors 11a, 11b. Accordingly, the light entering from the forward (from above as viewed in FIG. 2) does not reach the peripheral portions of the photocathode surfaces 8. A resultant problem is that parts of the photocathode surfaces cannot be efficiently used. Further, in this arrangement, a most part of light entering the dead spaces 10a, 10b is reflected forward, and only a part of the light enters the photocathode surfaces 8. A resultant problem is that use efficiency of light is low.

Also, a method for eliminating dead spaces by means of using photomultipliers 4' whose photocathode surfaces 8' are hexagonal as in FIG. 4, or quadrangle although not shown is well known. This method can eliminate dead spaces among the photomultipliers 4'. However, it cost more to fabricate hexagonal or quadrangle photomultipliers 4' than to fabricate photomultipliers 4 with the circular photocathode surfaces 8. Further, even in the case that hexagonal photomultipliers 4' are used, dead spaces 10' among the lead housing 2' and the photomultipliers 4' cannot be eliminated.

Japanese Patent Laid-Open Publication No. 2-304316 (304316/1990) describes a high sensitivity photometering device including photomultipliers comprising a cylindrical transparent vessel having all the circumferential wall formed in a photocathode surface. This device is for efficiently collecting light from the sides of the photomultiplier. Accordingly, means for solving the problem of the dead spaces defined in the photomultiplier assembly is not described and taught in Japanese Patent Laid-Open Publication No. 2-304316.

SUMMARY OF THE INVENTION

An object of the present invention is to provide a photomultiplier assembly which can use light entering dead spaces defined in the photomultiplier assembly.

Another object of the present invention is to provide a photomultiplier assembly which can facilitate the assembling the photomultiplier assembly, and can improve positioning precision of the respective photomultipliers.

Further, another object of the present invention is to provide a gamma camera which can detect gamma rays with high sensitivity.

Accordingly, the present invention is directed to a photomultiplier assembly comprising: (a) a two-dimensional array of head-on type photomultipliers disposed in parallel with one another and on the same level, and having dead spaces defined among the photomultipliers, each of the photomultipliers including: (i) a transparent tubular closed vessel, (ii) a principal photocathode surface formed on an inside of an end plate on one end of the closed vessel, (iii) an electron multiplying unit disposed in the closed vessel for multiplying electrons emitted from the principal photocathode surface when the principal photocathode surface receives light entering the end plate, (iv) a convergent electrode having an opening for converging the electrons emitted from the principal photocathode surface and guiding the electrons to the electron multiplying unit, the convergent electrode being disposed between the principal photocathode surface and the electron multiplying unit, and (v) a side photocathode surface formed on a substantially entire circumferential inside surface of a side wall of the closed vessel in a predetermined region adjacent to the principal photocathode surface; and (b) reflectors disposed in the dead spaces respectively, each of the reflectors having reflecting surfaces for reflecting light which has entered in the dead space to the side photocathode surface of one of the photomultipliers nearest to an incidence point of the light.

When the closed vessels of the photomultipliers are substantially circular cylindrical, outer side surfaces of the closed vessels of a pair of the photomultipliers which are adjacent to each other contact with each other, whereby one of the dead spaces is defined by three of the photomultipliers which are adjacent to one another. In this case, each of the reflectors has a substantially triangular pyramidal shape having three inclined side surfaces as the reflecting surfaces, and it is disposed in one of the dead spaces with the reflecting surfaces faced respectively to the side photocathode surfaces of the three photomultipliers defining the corresponding dead spaces.

Also, the present invention relates to a gamma camera head comprising: (a) a lead housing having an opening formed in one side thereof; (b) a collimator disposed in the opening; (c) a scintillator disposed adjacent to the collimator in the lead housing for receiving gamma rays which have passed through the collimator and for emitting light; (d) a two-dimensional array of head-on type photomultipliers disposed in parallel with one another and on the same level in the lead housing, and having dead spaces defined among the photomultipliers, each of the photomultipliers including: (i) a transparent tubular closed vessel, (ii) a principal photocathode surface formed on an inside of an end plate on one end of the closed vessel, and faced to the scintillator, (iii) an electron multiplying unit disposed in the closed vessel for multiplying electrons emitted from the principal photocathode surface when the principal photocathode surface receives light entering the end plate, (iv) a convergent electrode having an opening for converging the electrons emitted from the principal photocathode surface and guiding the electrons to the electron multiplying unit, the convergent electrode being disposed between the principal photocathode surface and the electron multiplying unit, and (v) a side photocathode surface formed on a substantially entire circumferential inside surface of a side wall of the closed vessel in a predetermined region adjacent to the principal photocathode surface; (e) a light guide disposed between the photomultipliers and the scintillator in the lead housing for guiding light generated in the scintillator to the photomultipliers; and (f) reflectors disposed in the dead spaces respectively, each of the reflectors having reflecting surfaces for reflecting light which has entered in the dead space to the side photocathode surface of one of the photomultipliers nearest to an incidence point of the light.

The present invention will become more fully understood from the detailed description given hereinbelow and the accompanying drawings which are given by way of illustration only, and thus are not to be considered as limiting the present invention.

BRIEF DESCRIPTION OF THE DRAWINGS

In the course of the following detailed description, reference will be made to the attached drawings in which.

DETAILED DESCRIPTION OF THE PREFERRED EMBODIMENTS

Figure 1:
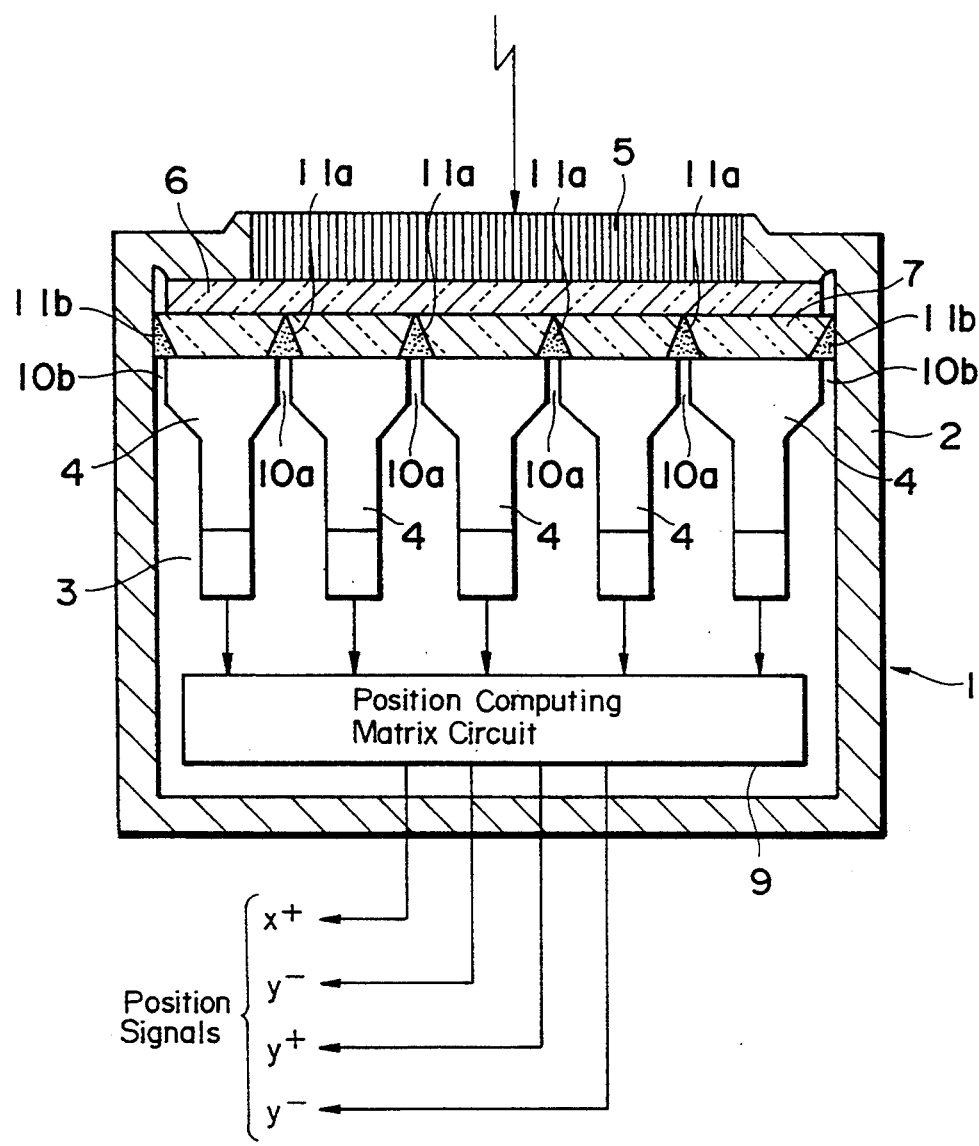
FIG. 1 is a vertical sectional view schematically showing the structure of a conventional gamma camera head.
Figure 2:
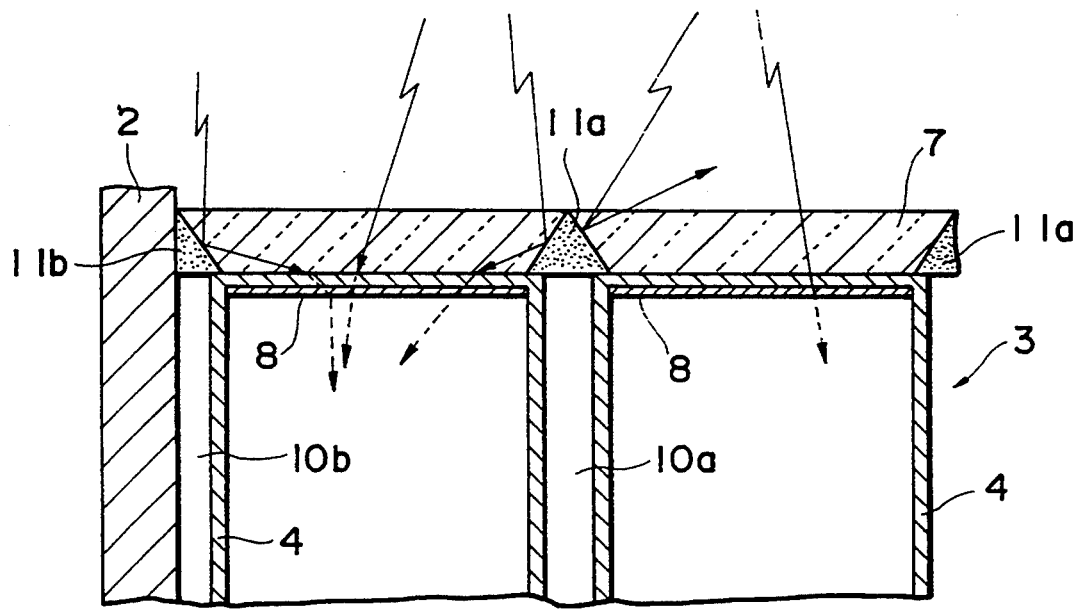
FIG. 2 is an enlarged sectional view schematically showing a part of the gamma camera head of FIG. 1.
Figure 3:
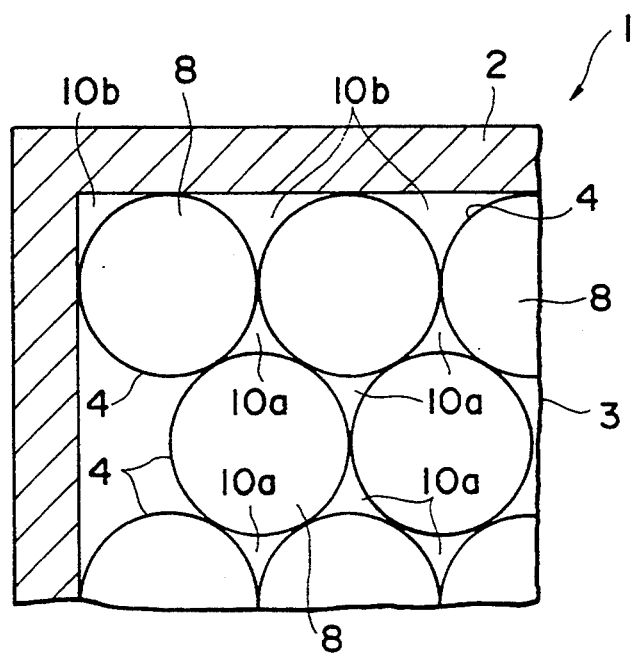
FIG. 3 is a partial transverse sectional view of the conventional gamma camera head, showing a photomultiplier assembly including photomultipliers with circular photocathode surfaces.
Figure 4:
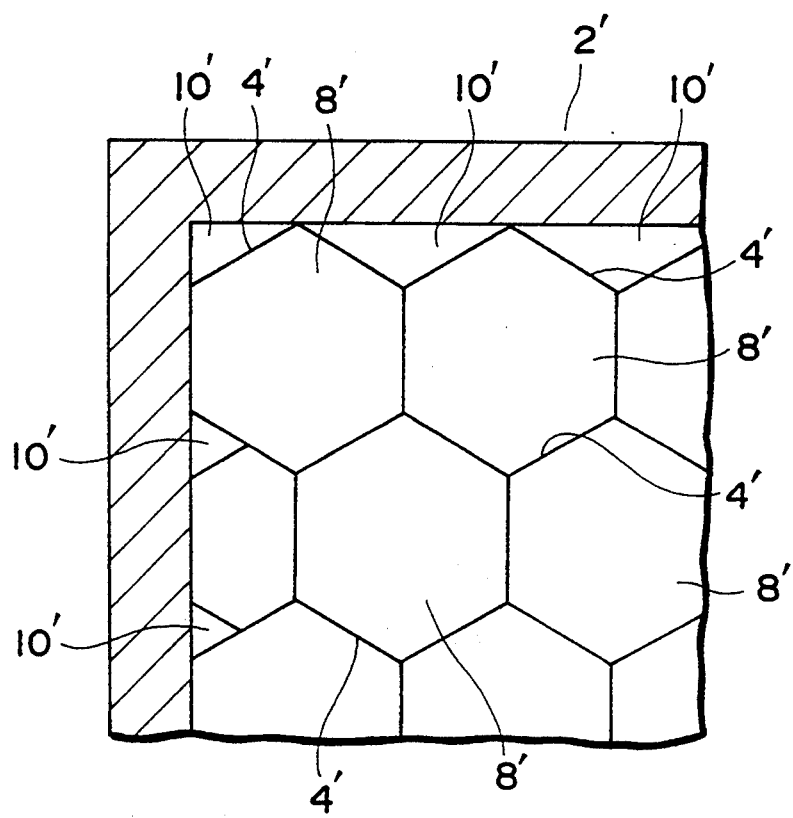
FIG. 4 is a partial transverse sectional view of the conventional gamma camera head, showing a photomultiplier assembly including photomultipliers with hexagonal photocathode surfaces.

Preferred embodiments of the present invention will be explained in good detail with reference to the drawings attached hereto. In the following description, like reference characters designate like or corresponding parts throughout the several views. Also in the following description, it is to be understood that such terms as "forward", "rearward", "upwardly", "downwardly", and the like, are words of convenience and are not to be construed as limiting terms.

Figure 5:
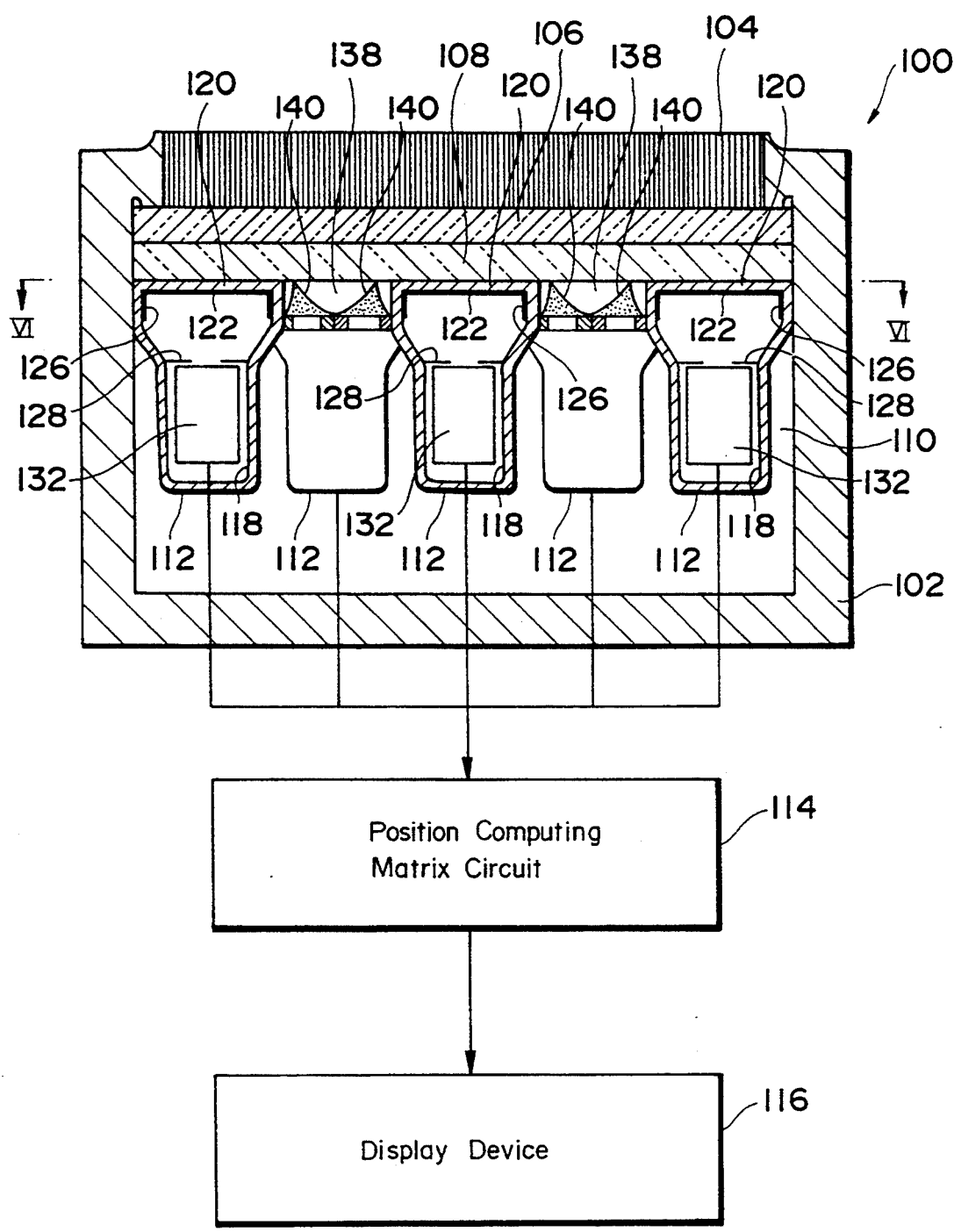
FIG. 5 is a vertical sectional view, along the line V—V in FIG. 6, of the gamma camera head including the photomultiplier assembly according to the present invention.

Referring now to the drawings, and particularly, to FIG. 5, there is shown a constructional view of a gamma camera for giving a distribution image of radioisotope supplied into a body, especially a detection unit of the gamma camera or a gamma camera head according to the present invention, being generally designated by the numeral 100. The gamma camera head 100 basically includes a one-side opened box-type lead shield or lead housing 102. In the opened side, there is provided a collimator, preferably a multi-hole collimator 104. In this embodiment, the multi-hole collimator 104 has a great number of small holes formed in a lead plate in parallel relation to one another.

On the side of the, back of the collimator 104 (underside of the collimator 104 in FIG. 5), there is provided a plate-type scintillator of, e.g., sodium iodide (NaI). This scintillator 106 is held in the lead housing 102 in parallel relation to the collimator 104 in such a manner as to cover the entire collimator 104. Furthermore, on the side of the back of the scintillator 106, there is provided a transparent and plate-shaped light guide 108 of e.g., acrylic resin or others. The light guide 108 is bonded to the scintillator 106 by transparent silicone grease or other suitable adhesives.

A photomultiplier assembly 110 according to this invention which will be described later in detail is provided in the lead housing 102 on the side of the back of the light guide 108. The photomultiplier assembly 110 comprises a plurality of photomultipliers 112 laterally disposed in an organized array (see FIG. 6).

Output signals from the respective photomultipliers 112 are supplied to a position computing matrix circuit 114 to compute gamma ray emitting positions. In this embodiment, the position computing matrix circuit 114 is provided outside the lead housing 102, but may be provided inside the position computing matrix circuit 114. An output signal from the position computing matrix circuit 114 is supplied to a display device, such as an X-Y oscilloscope, or others, and luminescent points are formed at positions on the screen corresponding to the gamma ray emitting points. It is preferred that the display device 116 can synthesize luminescent points generated in a certain period to display a distribution image on the screen. The basic structure of such gamma camera is conventionally known.

Then, the photomultiplier assembly 110 according to the present invention will be explained in further detail with reference to FIGS. 5 to 7. The photomultiplier assembly 110 includes a plurality of head-on or end-on photomultipliers 112. The photomultipliers 112 have the same configuration, and each of the photomultipliers includes a transparent closed vessel of a substantially cylindrical shape, concretely a transparent glass bulb 118 having both ends closed. As seen in FIG. 7, this glass bulb 118 has a larger diameter at the head portion or the upper portion thereof than the lower portion thereof. The upper end plate of the glass bulb 118 is circular and functions as a light entering window 120. A photo cathode surface 122 (hereinafter called "principal photocathode surface") is formed on the inside surface of the light entering window 120.

The photocathode surface is a film of photoemitter, which is made of antimony (Sb) and an alkali metal (e.g., cesium (Cs), potassium (K), rubidium (Rb) or others), or made of tellurium (Te) and an alkali metal. The photoemitter film is deposited over the entire inside surface of the glass bulb 118. Also, on the entire inside surface of the side wall of the glass bulb 118, there is formed a ring-shaped aluminum vapor-deposited film 124 for maintaining a potential of the photocathode surface. This aluminum deposited film 124 defines a part which functions as the photocathode surface. As seen in FIG. 7, according to the present invention, the upper end of the aluminum deposited film 124 is in a position which is below the light entering window 120 by a set distance. Accordingly, the peripheral portion of the principal photocathode surface is extended downward along the inside surface of the side wall of the glass bulb 118. The extended portion provides a side photocathode surface 126. In FIG. 7, the part of the photoemitter film which does not function as the photocathode surface 122, 126 are omitted.

A convergent electrode 128 is disposed inside the glass bulb 118 and at a position where it is opposed to the light entering window 120. The convergent electrode 128 has an opening 130, toward which photoelectrons from the principal photocathode surface 122 and the side photocathode surface 126 are converged and through which the photoelectrons are led to an electron multiplying unit 132.

There are various types of electron multiplying unit 132 which can be employed herein. In this embodiment, a plurality of stages of box-and-grid type dynodes 134a–134g are used. The photoelectrons are successively multiplied by the electron multiplying unit 132 by secondary electron emission effect to be taken out from an anode 136 as pulse signals.

Figure 6:
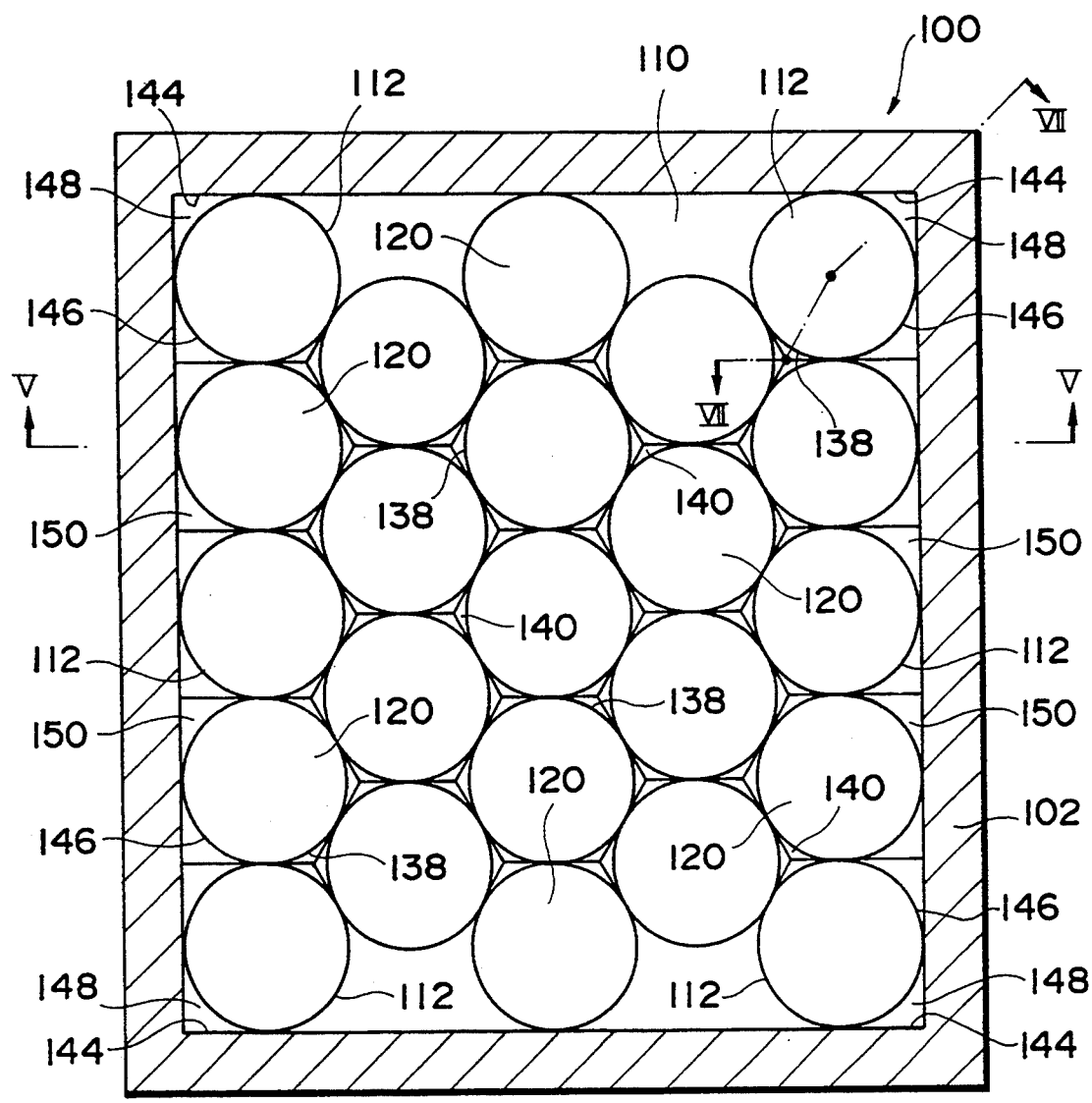
FIG. 6 is a transverse sectional view of the gamma camera head along the line VI—VI in FIG. 5.
Figure 7:
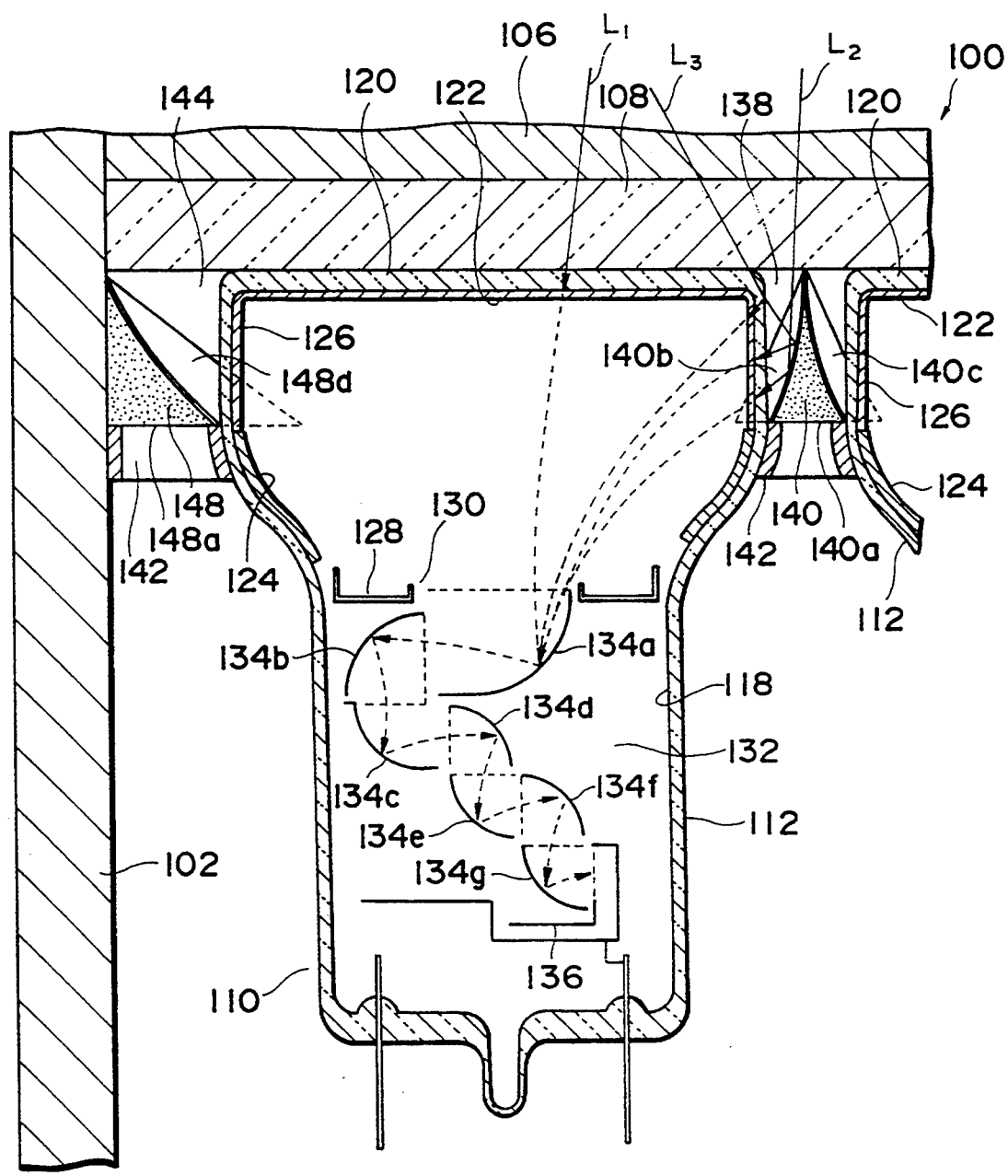
FIG. 7 is an enlarged sectional view, along the line VII—VII in FIG. 6, of a part of the gamma camera head of FIG. 5.

As shown in FIG. 6, a plurality of such photoelectron multipliers 112 are arranged two-dimensionally in a closest state to constitute the photomultiplier assembly 110. More specifically, the photomultipliers 112 are arranged such that their longitudinal axes are parallel to one another. Further, the photomultipliers 112 are arranged in a hexagon array or in a honeycomb array with the outside surfaces of the side walls of the glass bulbs 118 of adjacent ones of the photomultipliers contacting with each other. The outside surfaces (the upper surface in FIGS. 5 and 7) of the light entering windows 120 of the respective photomultipliers 112 are positioned in the same plane. The upper surfaces of the light entering windows 120 are bonded to the underside of the light guide 108 by transparent grease or a suitable adhesive. The inside surface of the side wall of the lead housing 102 encloses the photomultiplier assembly 110 in contact with the outside surfaces of the side walls of the glass bulbs 118 of those of the photomultipliers 112 located at the outer peripheral portion.

Figure 8:
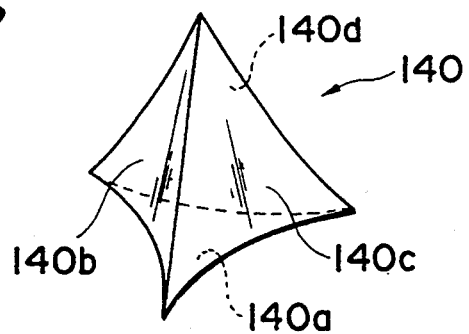
FIG. 8 is a perspective view of one example of a reflector disposed in each of dead spaces defined among photomultipliers of the photomultiplier assembly.

As shown in FIG. 6, such a photomultiplier assembly 110 has gaps or dead spaces 138 defined among the photomultipliers 112. Reflectors 140 are provided in respective dead spaces 138. As shown in FIG. 8, each reflector 140 has a substantially triangular pyramidal shape having a base surface 140a and three inclined side surfaces 140b, 140c, 140d. These inclined surfaces 140b, 140c, 140d have the same configuration and the same inclined angle to the base surface 140a. A reflector 140 is positioned in a dead space 138 with the base surface 140a located at substantially the same height as a boundary between the aluminum deposited film 124 and the side photocathode surface 126 and with the summit located at substantially the same height as the upper surfaces of the light entering windows 120 of the photomultipliers 112. Accordingly, the reflectors 140 do not interfere with the light guide 108, and it is not necessary to provide cuts or recesses in the light guide 108. The three inclined side surfaces 140b, 140c, 140d of each reflector 140 function as reflecting surfaces, and each reflecting surface is faced to the corresponding one of three of the photomultipliers which define the associated dead space 138. The respective base edges of each reflector 140 are curved so as to fit the side surface of the glass bulbs 118 of the associated photomultipliers without any gaps therebetween. Also, it is preferable that the edge portion of the base surface 140a of each reflector 140 is supported by a support member 142 disposed in the lower portion of the associated dead space 138.

The triangular pyramidal reflectors 140 are disposed in the respective dead spaces 138, so that light incident in the dead spaces 138 through the light guide 108 from the scintillator 106 are reflected on the reflecting surfaces 140b, 140c, 140d, and most of the reflected light enters the side photocathode surface 126 of the photomultiplier 112. Also, the reflectors 140 are disposed in the dead spaces 138, whereby the reflectors 140 function as spacers or assembling jibs in assembling the photomultiplier assembly 110, and the photomultiplier assembly 110 can be easily fabricated. Accordingly, the reflectors 140 contributes to the improvement of positioning precision of the photomultipliers 112, and the improvement of characteristics of the photomultiplier assembly 110 as a whole.

It will be noted that the reflecting surfaces 140b, 140c, 140d of each reflector 140 need not be always flat. It is preferable that vertical section of the reflecting surfaces 140b, 140c, 140d are so curved that reflected light on the reflecting surfaces 140b, 140c, 140d efficiently enter the side photocathode surface 126 of multipliers 112 adjacent to the reflecting surfaces 140b, 140c, 140d. Similarly, it is preferable that the reflecting surfaces 140b, 140d, 140d have suitably curved horizontal section, i.e., in a direction normal to a direction of height so that reflected light on the three reflecting surfaces 140b, 140c, 140d efficiently enter the side photocathode surfaces 126 of those of the photomultipliers adjacent to the reflecting surfaces 140b, 140c, 140d.

In detecting a distribution image of radioisotope given to a patient by the above-mentioned gamma camera head 100, the collimator 102 of the gamma camera head 100 is directed to a required area of the patient. Only those of gamma rays emitted from the radioisotope which propagate in parallel relation to the holes in the collimator 102 pass through the holes of the collimator 102. When the gamma rays arrive at the scintillator 104, light is generated in the scintillator 104, and the light passes the light guide 108 to advance to the photomultiplier assembly 110.

When light is incident on the principal photocathode surface 122 of the photomultiplier 112 (see the arrow $L_1$ in FIG. 7), photoelectrons are emitted from the principal photocathode surface 122. The photoelectrons are led to the electron multiplying unit 132 by the convergent electrode 128. In the electron multiplying unit 132 the photoelectrons are successively multiplied by secondary electron emitting effect and are captured by the anode 136, all in a well-known manner.

On the other hand, when light enters the dead spaces 138 among the photomultipliers 112, the light is reflected on the reflecting surfaces 140b, 140c 140d of the reflectors 140 and enters the side photocathode surfaces 126 of the photomultipliers 112 (see the arrow $L_2$ in FIG. 7). As a result, photoelectrons are emitted from the side photocathode surfaces 126, the photoelectrons are led to the electron multiplying unit 132 by the convergent electrode 128 and are finally captured by the anode 136.

Further, when light enters the peripheral portion of the light entering window 120 of the photomultiplier 112 obliquely and outwardly as indicated by the arrow $L_3$ in FIG. 7, the light advances in the side wall of the glass bulb 118, and a part of the light is reflected on the outside surface of the side wall, the remaining part of the light advancing from the side wall into the dead space 138. The light which has entered the dead space 138 is reflected on the reflector 140 to enter the side photocathode surface 126. In the conventional structure as shown in FIG. 1, the light propagating toward the peripheral portion of the light entering window is blocked by the reflector 11, and is not used.

Thus, most of light entering from forward of the photomultiplier assembly 112 is converted into photoelectrons, and use efficiency of the entering light is accordingly improved.

Pulse signals taken out from the anode 136 of the respective photomultipliers 112 are supplied to the position computing matrix circuit 114 in the known manner, and positions of gamma ray emitting points are detected. Furthermore, detection results of the position computing matrix circuit 114 are inputted to the display device 116, and a distribution image of the radioisotope is displaced on the display device 116.

Figure 9:
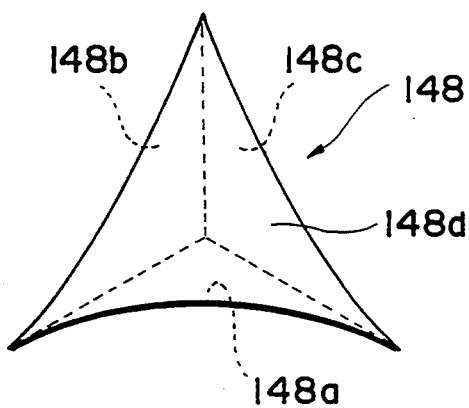
FIG. 9 is a perspective view of one example of a reflector disposed in each of dead spaces at the corners of the photomultiplier assembly.
Figure 10:
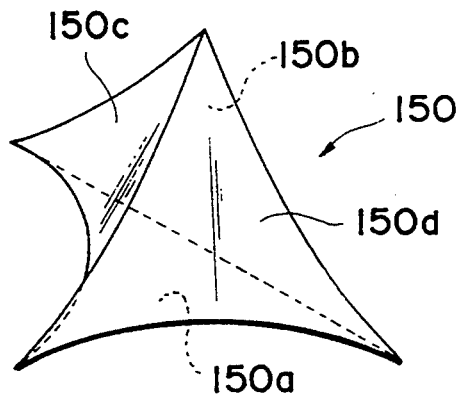
FIG. 10 is a perspective view of one example of a reflector disposed in each of dead spaces at the peripheral portion of the photomultiplier assembly.

Referring again to FIG. 6, dead spaces 114, 146 are defined between the photomultiplier assembly 110 and the lead housing 102. To improve use efficiency of the incident light still more, it is preferred to dispose suitable reflectors also in these dead spaces 144, 146. Reflectors 148 of FIG. 9 are disposed in the dead spaces 144 at the corner portions. Each reflector 148 has a substantially triangular pyramidal shape including a base surface 148a, two side surfaces 148b, 148c which are normal to the base surface 148a and normal to each other, and an inclined surface 148d. The inclined side surface 148d serves as a reflecting surface. Each reflector 148 is positioned with the side surfaces 148b, 148c contacting the inside surface of the lead housing 102, and the inclined surface 148d is faced to one of the photomultipliers 112 at a corner. Preferably, the reflectors 150 disposed in the dead spaces 146 defined with respect to the inside surface of the side wall of the lead housing 102 have the configuration as shown in FIG. 10. Each of these reflectors 150 has a base surface 150a, one side surface 150b to be contacted with the inside surface of the lead housing 102, and two inclined surfaces 150c, 150d. Each inclined surface 150c, 150d serves as reflecting surface for reflecting light to one of the photomultipliers 112 adjacent to it.

Figure 11:
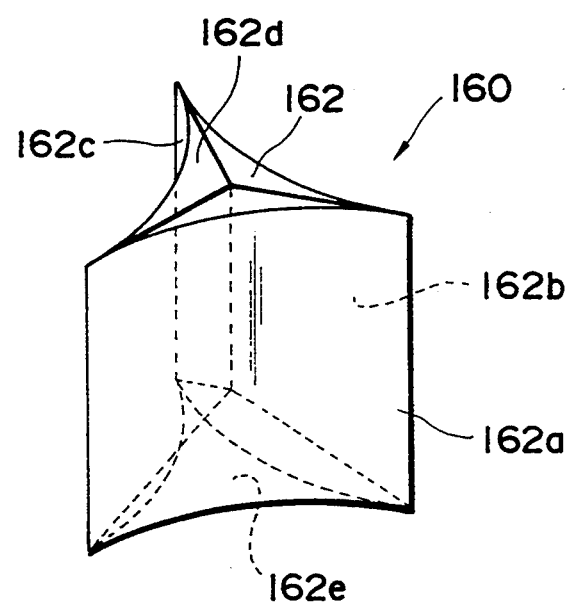
FIG. 11 is another example of a reflector disposed in each of dead spaces defined among photomultipliers.
Figure 12:
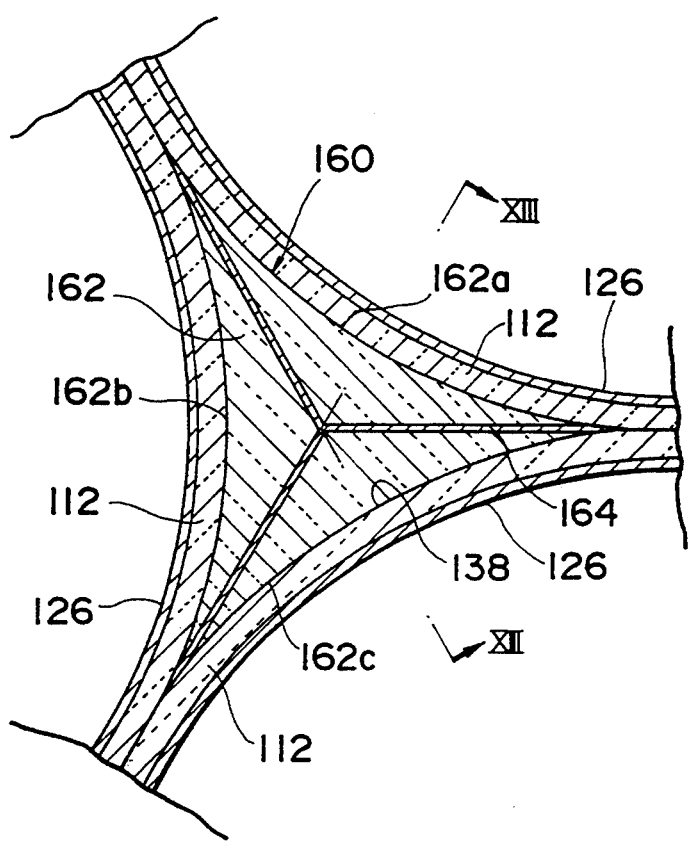
FIG. 12 is a transverse sectional view of a part of the photomultiplier assembly, along the line XIII—XIII in FIG. 13, in a state in which reflectors of FIG. 11 are disposed in dead spaces among the photomultipliers, respectively.
Figure 13:
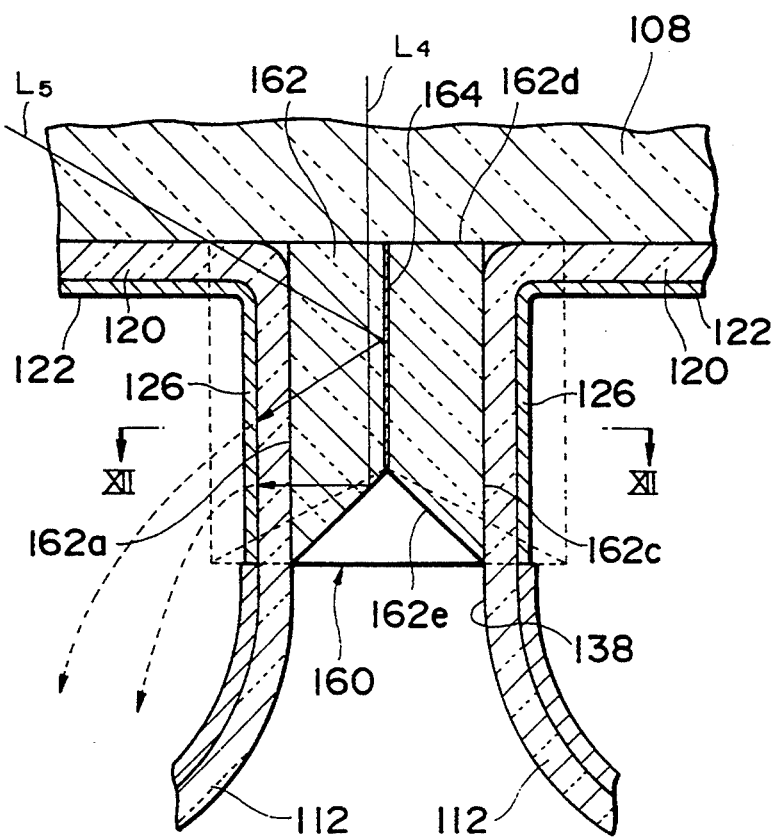
FIG. 13 is a sectional view along the line XIII—XIII of FIG. 12.

In the above-mentioned embodiment, the shape of the reflectors disposed in the photomultiplier assembly is substantially triangular pyramidal. However, it is not necessary that the shape of the reflector is triangular pyramidal as long as the reflector can reflect light to one of the photomultipliers nearest to a light incident point. For example, as shown in FIG. 11, a substantially triangular prismatic reflector which has a predetermined length may be used. As shown in FIGS. 12 and 13, reflectors 160 of FIG. 11 are disposed in the dead spaces 138 among photomultipliers 112. The main body 162 of each reflector 160 is made of a transparent material. Three side surfaces 162a, 162b, 162c of the reflector main body 162 are formed in concave surfaces in the form of cylindrical surface. The side surfaces 162a, 162b, 162c contact the side surfaces of their corresponding photomultipliers 112, respectively, without any gap. The upper surface 162d of the reflector main body 162 is plane, and is located in the same plane as the upper surfaces of the light entering windows 120 of the photomultipliers 112 when the reflector main body 162 is set in a predetermined position. The bottom surface 162e of the reflector body 162 is a concave surface in the shape of a substantially triangular pyramid. A reflecting material is applied on the concave bottom surface so that the side of the bottom surface 168e faced to the reflector main body 162 acts as the reflecting surface. Accordingly, when light enters the upper surface 162d of the reflector main body 162 and travels downwardly along the axis of the main body 162, the light is laterally reflected by the reflecting surface 162e (see the arrow $L_4$ in FIG. 13).

Also, thin reflecting plates 164 having both surfaces formed in reflecting surfaces are buried in the reflector body 162 respectively at positions of planes defined by the central axis and the respective side edges.

When such triangular prismatic reflectors 160 are disposed in the dead spaces 138 among the photomultipliers 112, light entering the dead spaces 138 is reflected on the reflecting plates 164 or the bottom reflecting surfaces 162e and enters the side photocathode surfaces 126 of the corresponding photomultipliers 112. In the case that the reflectors 140 of FIG. 8 are used, light entering the dead spaces 138 obliquely is not reflected by the reflectors 140 and passes by the reflectors 140. But in the case that the substantially triangular cylindrical reflectors 160 are used, all of light which has entered the dead spaces 138 can be reflected, with a result that use efficiency of light can be improved (see the arrow $L_5$ in FIG. 13). Further, as the substantially triangular cylindrical reflectors 160 contact the photomultipliers 112 at larger areas, they can be easily disposed in the dead spaces 138. In addition, in the case that the upper surfaces 162d of the reflectors 160 are positioned in the same plane as the light entering windows 120 of the photomultipliers 112, the reflectors 160 can be bonded to the light guide 108 by, e.g., grease. Therefore, the support members 142 in FIGS. 5 and 7 are not necessary. Also, the reflectors 160 is superior to the triangular pyramidal reflectors 140 in the function as spacers in assembling the photomultiplier assembly 110.

Figure 14:
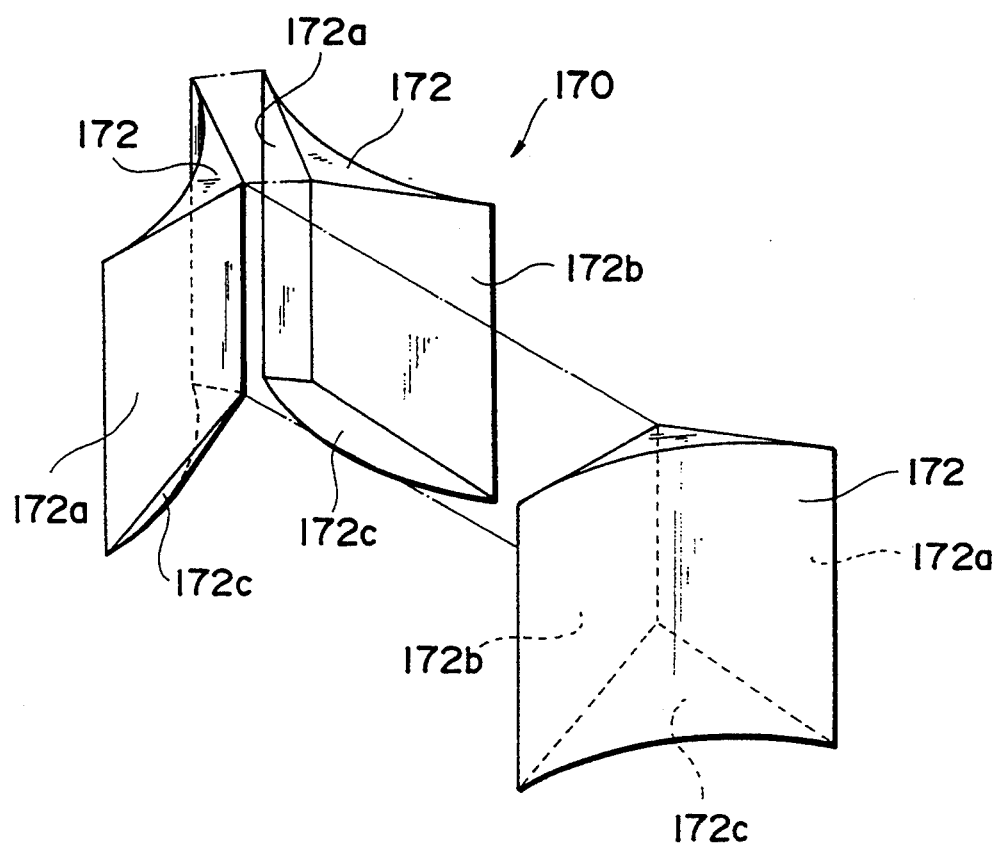
FIG. 14 is a exploded perspective view of another example of a reflector disposed in each of dead spaces defined among the photomultipliers.

Each of the above-mentioned reflectors 160 is molded in one-piece, but instead three reflector parts 172 in FIG. 14 may be assembled in a reflector 170. This reflector 170 also produces the same effect as the reflector 160. Each reflector part 172 has a shape identical to a part of a reflector 160 divided along planes defined by the central axis and the respective side edges. And, a reflecting material is coated over two plane side surfaces 172a, 172b and a bottom surface 172c. Thus, structures and shapes of the reflectors are not limited to those of the above-mentioned embodiments.

Figure 15:
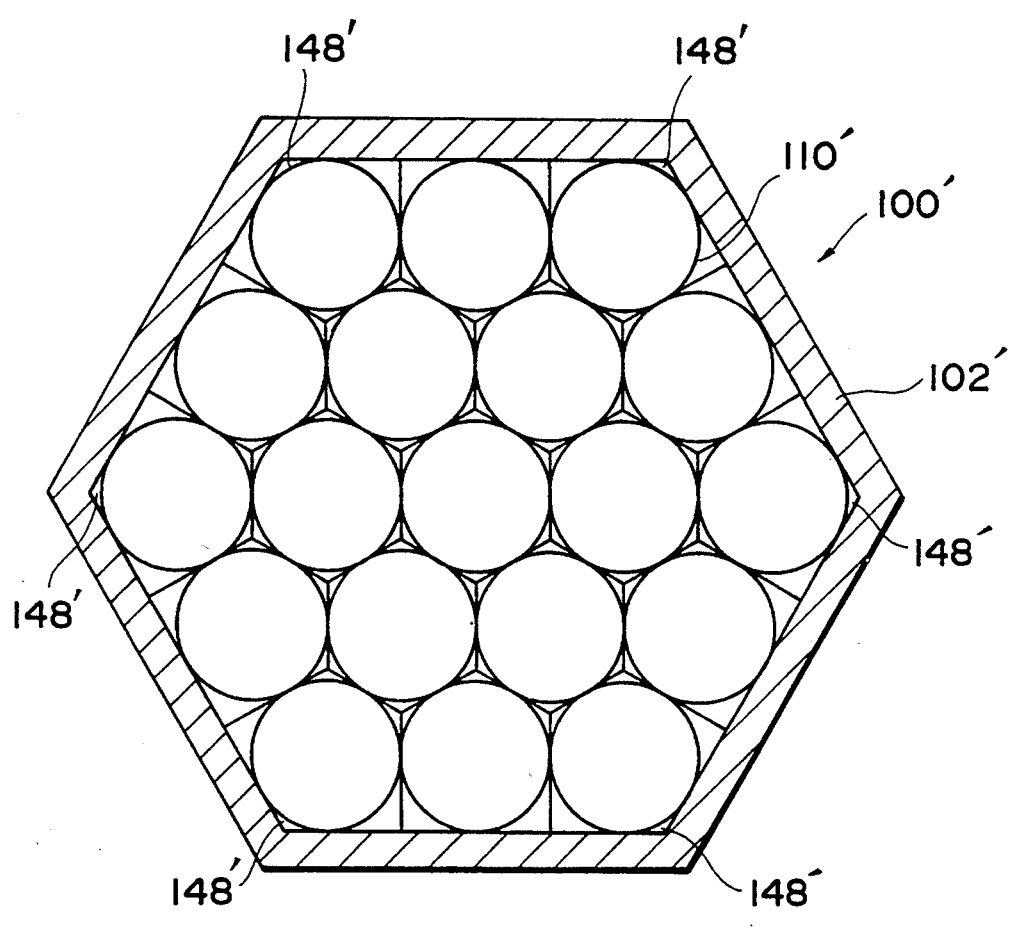
FIG. 15 is a transverse sectional view of the gamma camera head including the photomultiplier assembly having hexagonally arranged photomultipliers.
Figure 16:
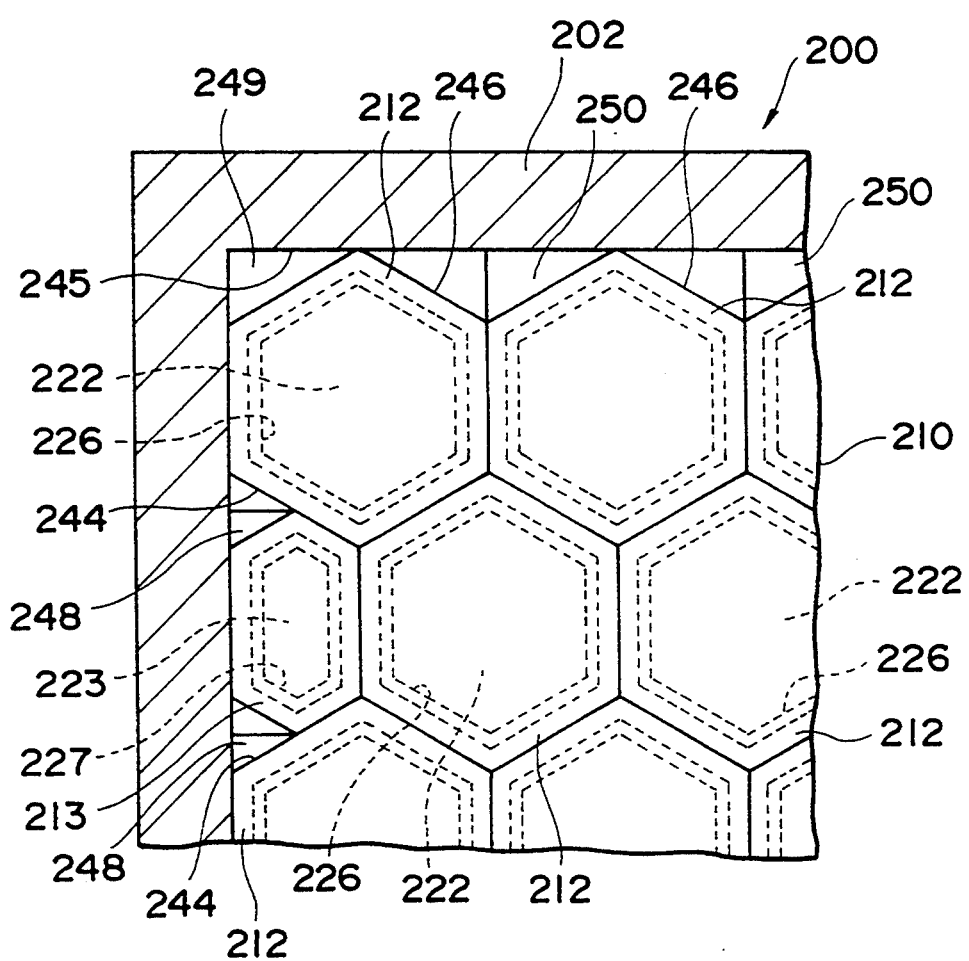
FIG. 16 is a transverse sectional view of a part of the gamma camera head including a photomultiplier assembly having photomultipliers with hexagonal photocathode surfaces.

It will be appreciated that various changes may be made in the arrangement of photomultiplier assembly. For example, a hexagonal arrangement of the photomultiplier assembly 110' of FIG. 15 can be used. In this case, a housing 102' of a gamma camera head 100' has an interior space of hexagonal horizontal or lateral cross-section. As a matter of course to those skilled in the art, shapes of reflectors which are disposed in dead spaces 148' at the corners are varied suitably in accordance with shapes of the dead spaces 148'. The other structure of the hexagonal gamma camera head 100' is the same as the gamma camera head 100 in FIGS. 5 to 7. FIG. 16 shows a part of the photomultiplier assembly, generally designated 210, comprising photomultipliers having hexagonal photocathode surfaces, i.e., hexagonal heads. In the photomultiplier assembly 210 of FIG. 16, photomultipliers 212 having substantially regular hexagonal photocathode surfaces 222, and photomultipliers 213 having irregular hexagonal photocathode surfaces 223 so that dead spaces are minimized when the assembly 210 is housed in a lead housing 202 of a gamma camera head 200, an interior space of which is rectangular in horizontal section. In such photomultiplier assembly 210, no dead spaces are formed among the photomultipliers 212, 213. But even by the use of such photomultipliers 212, 213, dead spaces 244, 245, 246 are formed between the photomultiplier assembly 210 and the inside surface of the housing 202. To use light entering these dead spaces 244, 245, 246, according to the present invention, reflectors 248, 249, 250 are disposed in respective dead spaces 244, 245, 246, and side photocathode surfaces 226, 227 extended downward from the edges of hexagonal principal photocathode surfaces 222, 223 are formed in the respective photomultipliers 212, 213 as in the photomultipliers 112 having the circular photocathode surfaces 122 of FIG. 7.

In the arrangement of FIG. 16, three kinds of dead spaces 244, 245, 246 having different sizes are formed. Triangular pyramidal reflectors of FIG. 17 can be disposed in the dead spaces 244 defined by the photomultipliers 213 having irregular hexagonal photocathode surfaces 223, photomultipliers 212 having regular hexagonal photocathode surfaces 222, and the inside surface of a housing 202. Each of the reflectors 248 has a side surface 248b normal to a base surface 248a, and two inclined surfaces 248c, 248d. The inclined surfaces 248c, 248d are reflecting surfaces. When a reflector 248 is set in position in the associated dead space 244, the side surface 248c contacts the inside surface of the housing 202, and the reflecting surfaces 248c, 248d can reflect light entering the dead space 244 to the corresponding photomultipliers 212, 213. The reflected light enters the side photocathode surfaces 226, 227 of the photomultipliers 212, 213 to be converted into photoelectrons.

Figure 18:
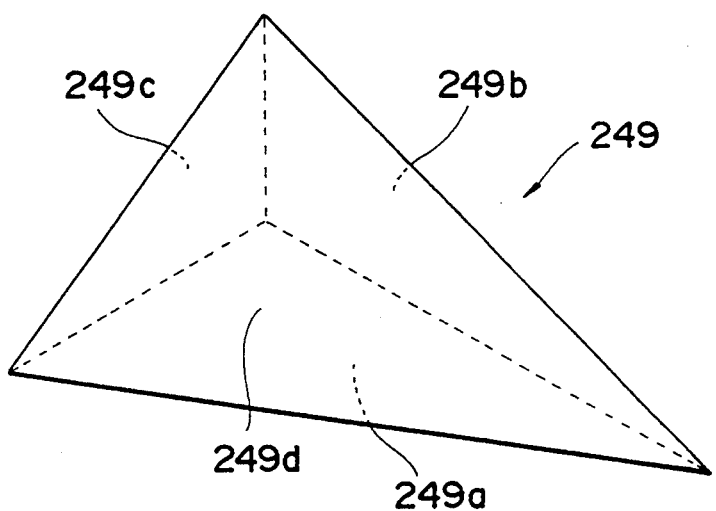
FIG. 18 is a perspective view of one example of a reflector disposed in each of dead spaces formed in the photomultiplier assembly of FIG. 16, which are different from the above-mentioned dead spaces.

Reflectors 249 of FIG. 18 are disposed the dead spaces 245 at the corners. Each of the reflectors 249 has two side surfaces 249b, 249c which are normal to a base surface 249a and normal to each other, and one inclined surface 249d. The inclined surface 249d is a reflecting surface for reflecting light to the corresponding photomultiplier 212 at a corner.

Figure 19:
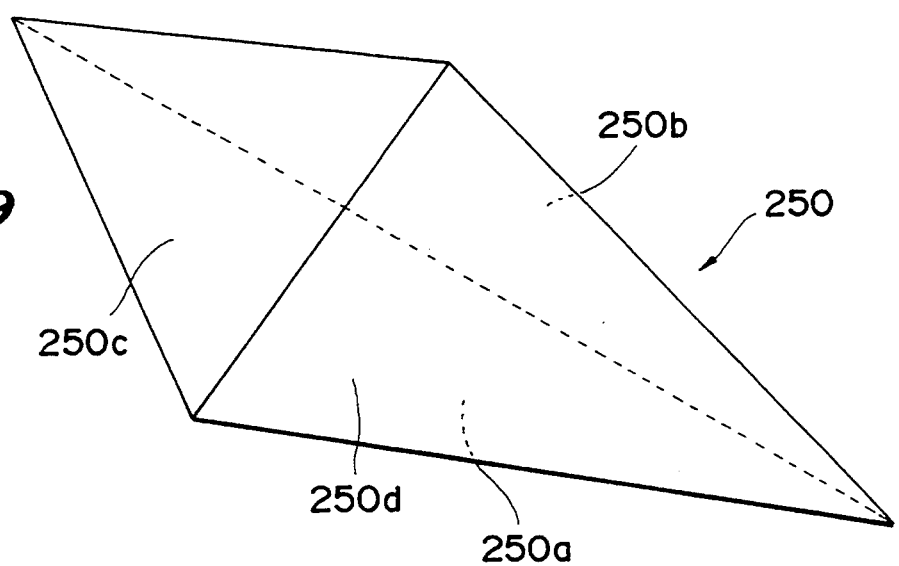
FIG. 19 is a perspective view of one example of a reflector disposed in each of dead spaces formed in the photomultiplier assembly of FIG. 16, which are different from the above-mentioned dead spaces.

Reflectors 250 of FIG. 19 are disposed in dead spaces 246 defined between two photomultipliers 212 having regular hexagonal photocathode surfaces 222, and the inside surface of the housing 202. Each of the reflectors 250 has a side surface 250b normal to a base surface 250a, and two inclined surfaces 250c, 250d, and the inclined surfaces 250c, 250d are reflecting surfaces.

Figure 17:
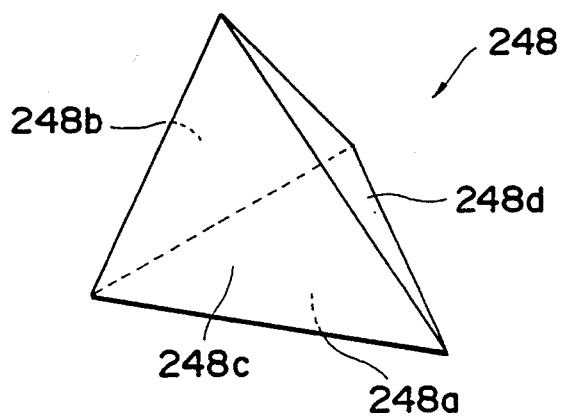
FIG. 17 is a perspective view of one example of a reflector disposed in each of dead spaces formed in the photomultiplier assembly of FIG. 16.

The reflecting surfaces of the reflectors 248, 249, 250 of FIGS. 17 and 18 are plane. But the reflecting surfaces may be suitably curved so as to reflect incident light to the side photocathode surfaces 226, 227 of the photomultipliers 212, 213. Shapes of the reflecting surfaces are not essentially triangular pyramidal, and although not shown, may have other shapes, such as triangular prism.

The above-mentioned embodiments relate to a gamma camera head, but the photomultiplier assembly according to the present invention is applicable to other devices, such as high sensitivity photometering devices for metering a position of feeble light.

It is thought that the present invention and many of its attendant advantages will be understood from the foregoing description and it will be apparent that various changes may be made in the form, construction and arrangement thereof without departing from the spirit and scope of the invention or sacrificing all of its material advantages, the form hereinbefore described being merely a preferred or exemplary embodiment thereof.

What is claimed is:

1. A photomultiplier assembly comprising:
   (a) a two-dimensional array of head-on type photomultipliers disposed in parallel with one another and on the same level, said array having dead spaces defined between said photomultipliers, each of said photomultipliers including:
      (i) a transparent tubular closed vessel having an end plate located at one end,
      (ii) a principal photocathode surface formed on an inside of said end plate of said closed vessel,
      (iii) an electron multiplying unit disposed in said closed vessel for multiplying electrons emitted from said principal photocathode surface when said principal photocathode surface receives light entering said end plate,
      (iv) a convergent electrode having an opening for converging electrons emitted from said principal photocathode surface and for guiding said electrons to said electron multiplying unit, said convergent electrode being disposed between said principal photocathode surface and said electron multiplying unit, and
      (v) a side photocathode surface formed on a substantially entire circumferential inside surface of a side wall of said closed vessel in a predetermined region adjacent to said principal photocathode surface;
   and
   (b) reflectors disposed in said dead spaces respectively, each of said reflectors having reflecting surfaces for reflecting light which has entered said dead space to one of said side photocathode surfaces of one of said photomultipliers nearest to an incidence point of said entering light.

2. A photomultiplier assembly according to claim 1, wherein said closed vessels of said photomultiplier are substantially circular and cylindrical, where outer side surfaces of closed vessels corresponding to a pair of adjacent photomultipliers contact each other, one of said dead spaces being defined by three of said photomultipliers which are adjacent to one another.

3. A photomultiplier assembly according to claim 1, including support means for supporting said reflectors at a predetermined position in said dead spaces, respectively.

4. A photomultiplier assembly according to claim 1, including an enclosing member for enclosing said two-dimensional array of said photomultipliers, said enclosing member, together with said array of said photomultipliers, defining a plurality of peripheral dead spaces; and peripheral reflectors disposed in the peripheral dead spaces respectively, each of said peripheral reflectors having a reflecting surface for reflecting light which has entered said peripheral dead space to said side photocathode surface of one of said photomultipliers nearest to an incidence point of said light.

5. A photomultiplier assembly according to claim 1, wherein each of said side photocathode surfaces is extended from a peripheral edge of said principal photocathode surface on said end plate to a predetermined level between said convergent electrode and said principal photocathode surface such that electrons emitted from said side photocathode surface are guided to said electron multiplying unit through said opening of said convergent electrode.

6. A photomultiplier assembly comprising:
   (a) a two-dimensional array of head-on type photomultipliers disposed in parallel with one another and on the same level, said array having dead spaces defined between said photomultipliers, each of said photomultipliers including:
      (i) a transparent tubular closed vessel having an end plate located at one end, said closed vessels of said photomultiplier being substantially circular and cylindrical, outer side surfaces of closed vessels corresponding to a pair of adjacent photomultipliers contacting each other, one of said dead spaces being defined by three of said photomultipliers which are adjacent to one another, (ii) a principal photocathode surface formed on an inside of said end plate of said closed vessel, (iii) an electron multiplying unit disposed in said closed vessel for multiplying electrons emitted from said principal photocathode surface when said principal photocathode surface receives light entering said end plate, (iv) a convergent electrode having an opening for converging electrons emitted from said principal photocathode surface and for guiding said electrons to said electron multiplying unit, said convergent electrode being disposed between said principal photocathode surface and said electron multiplying unit, and (v) a side photocathode surface formed on a substantially entire circumferential inside surface of a side wall of said closed vessel in a predetermined region adjacent to said principal photocathode surface;

and (b) reflectors disposed in said dead spaces respectively, each of said reflectors having reflecting surfaces for reflecting light which has entered said dead space to one of said side photocathode surfaces of one of said photomultipliers nearest to an incidence point of said entering light, where each of said reflectors has a substantially triangular pyramidal shape with three inclined side surfaces as said reflecting surfaces, said reflectors being disposed in one of said dead spaces with said reflecting surfaces faced respectively to said side photocathode surfaces of said three photomultipliers defining one of said dead spaces.

7. A photomultiplier assembly according to claim 6, wherein summits of said reflectors are positioned on a level substantially the same as a level of the outside surfaces of said end plates of said photomultipliers, and wherein base surfaces of said reflectors are positioned on a predetermined level within an extent of said side photocathode surfaces of said photomultipliers.

8. A photomultiplier assembly according to claim 6, wherein a shape of the base surface of said reflector substantially agrees with a cross-sectional shape of said dead space.

9. A photomultiplier assembly comprising:

(a) a two-dimensional array of head-on type photomultipliers disposed in parallel with one another and on the same level, said array having dead spaces defined between said photomultipliers, each of said photomultipliers including:

(i) a transparent tubular closed vessel having an end plate located at one end, said closed vessels of said photomultiplier being substantially circular and cylindrical, outer side surfaces of closed vessels corresponding to a pair of adjacent photomultipliers contacting each other, one of said dead spaces being defined by three of said photomultipliers which are adjacent to one another, (ii) a principal photocathode surface formed on an inside of said end plate of said closed vessel, (iii) an electron multiplying unit disposed in said closed vessel for multiplying electrons emitted from said principal photocathode surface when said principal photocathode surface receives light entering said end plate, (iv) a convergent electrode having an opening for converging electrons emitted from said principal photocathode surface and for guiding said electrons to said electron multiplying unit, said convergent electrode being disposed between said principal photocathode surface and said electron multiplying unit, and (v) a side photocathode surface formed on a substantially entire circumferential inside surface of a side wall of said closed vessel in a predetermined region adjacent to said principal photocathode surface;

and (b) reflectors disposed in said dead spaces respectively, each of said reflectors having reflecting surfaces for reflecting light which has entered said dead space to one of said side photocathode surfaces of one of said photomultipliers nearest to an incidence point of said entering light, wherein each of said reflectors includes a transparent and substantially triangular prismatic main body which is disposed in one of said dead spaces and which has the substantially same cross-sectional shape as said dead space, and a reflecting surface provided to said main body so that light incident on said main body can be reflected to said side photocathode surface of one of said photomultipliers nearest to an incidence point of said light.

10. A photomultiplier assembly comprising:

(a) a two-dimensional array of head-on type photomultipliers disposed in parallel with one another and on the same level, each of said photomultipliers including:

(i) a transparent tubular closed vessel having an end plate located at one end, (ii) a principal photocathode surface formed on an inside of said end plate of said closed vessel, (iii) an electron multiplying unit disposed in said closed vessel for multiplying electrons emitted from said principal photocathode surface when said principal photocathode surface receives light entering said end plate, (iv) a convergent electrode having an opening for converging electrons emitted from said principal photocathode surface and for guiding the electrons to said electron multiplying unit, said convergent electrode being disposed between said principal photocathode surface and said electron multiplying unit, and (v) a side photocathode surface formed on a substantially entire circumferential inside surface of a side wall of said closed vessel in a predetermined region adjacent to said principal photocathode surface;

(b) an enclosing member for enclosing said two-dimensional array of said photomultipliers, said enclosing member, together with said array of said photomultipliers, defining a plurality of peripheral dead spaces; and (c) a peripheral reflectors disposed in said peripheral dead spaces respectively, each of said peripheral reflectors having a reflecting surface for reflecting light which has entered said peripheral dead space to the side photocathode surface of one of said photomultipliers nearest to an incidence point of said light.

11. A photomultiplier assembly according to claim 10, wherein said closed vessels of said photomultipliers are substantially hexagonal cylindrical, outer side surfaces of said closed vessels of those of said photomultipliers which are adjacent to one another contact with each other substantially without any gap.

12. A gamma camera head comprising:
   (a) a lead housing having an opening formed in one said thereof;
   (b) a collimator disposed in said opening;
   (c) a scintillator disposed adjacent to said collimator in said lead housing for receiving gamma rays which have passed through said collimator and for emitting light based on said received gamma rays;
   (d) a two-dimensional array of head-on type photomultipliers disposed in parallel with one another and on the same level in said lead housing, where dead spaces are defined between said photomultipliers, each of said photomultipliers including:
      (i) a transparent tubular closed vessel having an end plate on one end,
      (ii) a principal photocathode surface formed on an inside of said end plate of said closed vessel and faced to said scintillator,
      (iii) an electron multiplying unit disposed in said closed vessel for multiplying electrons emitted from said principal photocathode surface when said principal photocathode surface receives light entering said end plate,
      (iv) a convergent electrode having an opening for converging the electrons emitted from said principal photocathode surface and for guiding the electrons to said electron multiplying unit, said convergent electrode being disposed between said principal photocathode surface and said electron multiplying unit, and
      (v) a side photocathode surface formed on a substantially entire circumferential inside surface of a side wall of said closed vessel in a predetermined region adjacent to said principal photocathode surface;
   (e) a light guide disposed between said photomultipliers and said scintillator in said lead housing for guiding light generated in said scintillator to said photomultipliers; and
   (f) reflectors disposed in said dead spaces respectively, each of said reflectors having reflecting surfaces for reflecting light which has entered in said dead space to said side photocathode surface of one of said photomultipliers nearest to an incidence point of said light.

13. A gamma camera head according to claim 12, wherein said closed vessels of said photomultipliers are substantially circular cylindrical, outer side surfaces of said closed vessels of a pair of said photomultipliers which are adjacent to each other contact with each other, whereby one of said dead spaces is defined by three of said photomultipliers which are adjacent to one another.

14. A gamma camera head according to claim 12, including support means for supporting said reflectors at a predetermined position in said dead spaces, respectively.

15. A gamma camera head according to claim 12, including peripheral reflectors which, when a plurality of peripheral dead spaces are defined between the inner surface of the side wall of said lead housing and said array of said photomultipliers, are disposed in said peripheral dead spaces respectively, each of said peripheral reflectors having reflecting surfaces for reflecting light which has entered said peripheral dead spaces to said side photocathode surfaces of one of the photomultipliers nearest to an incidence point of said light.

16. A gamma camera head comprising:
   (a) a lead housing having an opening formed in one said thereof;
   (b) a collimator disposed in said opening;
   (c) a scintillator disposed adjacent to said collimator in said lead housing for receiving gamma rays which have passed through said collimator and for emitting light based on said received gamma rays;
   (d) a two-dimensional array of head-on type photomultipliers disposed fin parallel with one another and on the same level in said lead housing, where dead spaces are defined between said photomultipliers, each of said photomultipliers including:
      (i) a transparent tubular closed vessel having an end plate on one end, said closed vessels of said photomultipliers being substantially circular and cylindrical, outer side surfaces of said closed vessels corresponding to a pair of said photomultipliers which are adjacent to each other and contacting each other, one of said dead spaces being defined by three of said photomultipliers which are adjacent to one another,
      (ii) a principal photocathode surface formed on an inside of said end plate of said closed vessel and faced to said scintillator,
      (iii) an electron multiplying unit disposed in said closed vessel for multiplying electrons emitted from said principal photocathode surface when said principal photocathode surface receives light entering said end plate,
      (iv) a convergent electrode having an opening for converging the electrons emitted from said principal photocathode surface and for guiding the electrons to said electron multiplying unit, said convergent electrode being disposed between said principal photocathode surface and said electron multiplying unit, and
      (v) a side photocathode surface formed on a substantially entire circumferential inside surface of a side wall of said closed vessel in a predetermined region adjacent to said principal photocathode surface;
   (e) a light guide disposed between said photomultipliers and said scintillator in said lead housing for guiding light generated in said scintillator to said photomultipliers; and
   (f) reflectors disposed in said dead spaces respectively, each of said reflectors having reflecting surfaces for reflecting light which has entered in said dead space to said side photocathode surface of one of said photomultipliers nearest to an incidence point of said light, wherein each of said reflectors has a substantially triangular pyramidal shape having three inclined side surfaces as said reflecting surfaces, and is disposed in one of said dead spaces with said reflecting surfaces faced respectively to said side photocathode surfaces of said three photomultipliers defining one of said dead spaces.

17. A gamma camera head according to claim 16, wherein summits of said reflectors are on the substantially same level as the outside surfaces of said end plates of said photomultipliers, and base surfaces of said reflectors are positioned on a predetermined level within an extent of said side photocathode surfaces of said photomultipliers.

18. A gamma camera head according to claim 16, wherein a shape of the base surface of said reflector substantially agrees with a cross-sectional shape of said dead space.

19. A gamma camera head comprising:
(a) a lead housing having an opening formed in one said thereof;
(b) a collimator disposed in said opening;
(c) a scintillator disposed adjacent to said collimator in said lead housing for receiving gamma rays which have passed through said collimator and for emitting light based on said received gamma rays;
(d) a two-dimensional array of head-on type photomultipliers disposed in parallel with one another and on the same level in said lead housing, where dead spaces are defined between said photomultipliers, each of said photomultipliers including:
  (i) a transparent tubular closed vessel having an end plate on one end, said closed vessels of said photomultipliers being substantially circular and cylindrical, outer side surfaces of said closed vessels corresponding to a pair of said photomultipliers which are adjacent to each other and contacting each other, one of said dead spaces being defined by three of said photomultipliers which are adjacent to one another,
  (ii) a principal photocathode surface formed on an inside of said end plate of said closed vessel and faced to said scintillator,
  (iii) an electron multiplying unit disposed in said closed vessel for multiplying electrons emitted from said principal photocathode surface when said principal photocathode surface receives light entering said end plate,
  (iv) a convergent electrode having an opening for converging the electrons emitted from said principal photocathode surface and for guiding the electrons to said electron multiplying unit, said convergent electrode being disposed between said principal photocathode surface and said electron multiplying unit, and
  (v) a side photocathode surface formed on a substantially entire circumferential inside surface of a side wall of said closed vessel in a predetermined region adjacent to said principal photocathode surface;
(e) a light guide disposed between said photomultipliers and said scintillator in said lead housing for guiding light generated in said scintillator to said photomultipliers; and
(f) reflectors disposed in said dead spaces respectively, each of said reflectors having reflecting surfaces for reflecting light which has entered in said dead space to said side photocathode surface of one of said photomultipliers nearest to an incidence point of said light, wherein each of said reflectors includes a transparent and substantially triangular prismatic main body which is disposed in one of said dead spaces and has the substantially same cross-sectional shape as said dead space has, and a reflecting surface provided to said main body so that light incident on said main body can be reflected to said side photocathode surface of one of said photomultipliers nearest to an incidence point of said light.

20. A gamma camera head comprising:
(a) a lead housing having an opening formed in one side thereof;
(b) a collimator disposed in said opening;
(c) a scintillator disposed adjacent to said collimator in the lead housing for receiving gamma rays which have passed through said collimator and for emitting light;
(d) a two-dimensional array of head-on type photomultipliers disposed in parallel with one another and on the same level in said lead housing, said array of said photomultipliers, together with said lead housing, defining a plurality of peripheral dead spaces,
each of said photomultipliers including:
  (i) a transparent tubular closed vessel,
  (ii) a principal photocathode surface formed on an inside of an end plate on one end of said closed vessel, and faced to said scintillator,
  (iii) an electron multiplying unit disposed in said closed vessel for multiplying electrons emitted from said principal photocathode surface when said principal photocathode surface receives light entering said end plate,
  (iv) a convergent electrode having an opening for converging the electrons emitted from said principal photocathode surface and for guiding the electrons to said electron multiplying unit, said convergent electrode being disposed between said principal photocathode surface and said electron multiplying unit, and
  (v) a side photocathode surface formed on a substantially entire circumferential inside surface of a side wall of said closed vessel in a predetermined region adjacent to said principal photocathode surface;
(e) a light guide disposed between said photomultipliers and said scintillator in said lead housing for guiding light generated in said scintillator to said photomultipliers; and
(f) peripheral reflectors disposed in said peripheral dead spaces respectively, each of said peripheral reflectors having a reflecting surface for reflecting light which has entered in said peripheral dead space to said side photocathode surface of one of said photomultipliers nearest to an incidence point of said light.

21. A gamma camera head according to claim 20, wherein said closed vessels of said photomultipliers are substantially hexagonal cylindrical, outer side surfaces of said closed vessels of those of said photomultipliers which are adjacent to one another contact with each other substantially without any gap.

* * * * *